(12) United States Patent
Daugirdas et al.

(10) Patent No.: US 10,443,668 B2
(45) Date of Patent: Oct. 15, 2019

(54) ORBITAL CLUTCH AND BRAKE ASSEMBLY FOR C-ARM OF IMAGING SYSTEM

(71) Applicant: General Electric Company, Schenectady, NY (US)

(72) Inventors: Kristofer Daugirdas, Salt Lake City, UT (US); John Matthew Simmons, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 266 days.

(21) Appl. No.: 15/488,846

(22) Filed: Apr. 17, 2017

(65) Prior Publication Data

US 2018/0298970 A1    Oct. 18, 2018

(51) Int. Cl.

| F16D 67/02 | (2006.01) |
|---|---|
| F16D 49/00 | (2006.01) |
| F16D 65/02 | (2006.01) |
| A61B 6/00 | (2006.01) |
| A61B 6/10 | (2006.01) |
| F16D 121/14 | (2012.01) |
| F16D 125/40 | (2012.01) |

(52) U.S. Cl.
CPC .............. *F16D 67/02* (2013.01); *A61B 6/105* (2013.01); *A61B 6/4405* (2013.01); *A61B 6/4441* (2013.01); *A61B 6/4476* (2013.01); *F16D 49/00* (2013.01); *F16D 65/028* (2013.01); *F16D 2121/14* (2013.01); *F16D 2125/40* (2013.01)

(58) Field of Classification Search
CPC ..... A61B 6/105; A61B 6/4405; A61B 6/4441; A61B 6/4476; F16D 2121/14; F16D 2125/40; F16D 49/00; F16D 65/028; F16D 67/02
See application file for complete search history.

(56) References Cited

U.S. PATENT DOCUMENTS

| 5,073,917 A | * | 12/1991 | Van Endschot ...... | A61B 6/4441 378/193 |
| 9,025,730 B2 | | 5/2015 | Barker et al. | |
| 2012/0314843 A1 | * | 12/2012 | Limmer ............... | A61B 6/4441 378/197 |

(Continued)

FOREIGN PATENT DOCUMENTS

| CN | 206080549 U | 4/2017 |
| JP | 3651520 B2 | 5/2005 |

OTHER PUBLICATIONS

U.S. Appl. No. 15/472,589, filed Mar. 29, 2017, David Ellis Barker, et al.

(Continued)

*Primary Examiner* — Mark R Gaworecki
(74) *Attorney, Agent, or Firm* — Fletcher Yoder, P.C.

(57) ABSTRACT

A device is provided. The device includes an orbital clutch and brake assembly configured to couple to a C-arm rotation device that enables the C-arm to rotate in an orbital direction relative to the C-arm rotation device. The orbital clutch and brake assembly includes a housing, a roller, and a brake pad. The roller and brake pad are disposed within the housing. The brake pad is configured to directly contact the roller and to not contact the C-arm when the orbital clutch and brake assembly applies a braking force to the C-arm.

17 Claims, 6 Drawing Sheets

(56) References Cited

U.S. PATENT DOCUMENTS

2013/0279663 A1\* 10/2013 Barker ................ A61B 6/4405
378/197

OTHER PUBLICATIONS

Extended European Search Report and Opinion issued in connection with corresponding EP Application No. 18167503.4, dated Sep. 17, 2018, 6 pages.

\* cited by examiner

ORBITAL CLUTCH AND BRAKE ASSEMBLY FOR C-ARM OF IMAGING SYSTEM

BACKGROUND

The subject matter disclosed herein relates to X-ray imaging systems having C-arms and, more particularly, to an orbital clutch and brake assembly for the C-arm.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm. In such cases, the C-arm can often be raised and lowered, be moved from side to side, and/or be rotated about one or more axes of rotation. For example, the C-arm may be rotated in an orbital direction. Devices may directly apply braking and/or drag (clutch) force to the C-arm affecting rotation of the C-arm in the orbital direction. These devices also utilize two different systems for both the brake and the clutch, which complicates the design, manufacturing and assembly of these devices. In addition, these devices do not account for variations along the C-arm.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, an X-ray imaging system is provided. The X-ray imaging system includes an X-ray radiation source, an X-ray detector, and a C-arm having the X-ray radiation source disposed on a first end and the X-ray detector disposed on a second end opposite the first end. The X-ray imaging system also includes a C-arm rotation device configured to enable the C-arm to rotate in an orbital direction relative to the C-arm rotation device. The X-ray imaging system further includes an orbital clutch and brake assembly coupled to the C-arm rotation device, wherein the orbital clutch and brake assembly is spring loaded into the C-arm and configured to apply both a drag force and a braking force on the C-arm that is consistent along the C-arm in the orbital direction regardless of variations in a cross-sectional profile of the C-arm in the orbital direction.

In accordance with a second embodiment, a device is provided. The device includes an orbital clutch and brake assembly configured to couple to a C-arm rotation device that enables the C-arm to rotate in an orbital direction relative to the C-arm rotation device. The orbital clutch and brake assembly includes a housing, a roller and a brake pad. The roller and brake pad are disposed within the housing. The brake pad is configured to directly contact the roller and to not contact the C-arm when the orbital clutch and brake assembly applies a braking force to the C-arm.

In accordance with a third embodiment, a device is provided. The device includes an orbital clutch and brake assembly configured to couple to a C-arm rotation device that enables the C-arm to rotate in an orbital direction relative to the C-arm rotation device. The orbital clutch and brake assembly includes a housing, multiple springs, a roller, and a brake pad. The roller and brake pad are disposed within the housing. The multiple springs are disposed on an outside of the housing. The multiple springs are configured to spring load the orbital clutch and brake assembly into the C-arm to enable the orbital clutch and brake assembly to apply both a drag force and a braking force on the C-arm that is consistent along the C-arm in the orbital direction regardless of variations in a cross-sectional profile of the C-arm in the orbital direction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe a device (e.g., orbital clutch and brake assembly) that provides a single system or assembly for providing both a braking force and a clutch force to a C-arm of an X-ray imaging system. The device may be disposed within a C-arm rotation device (e.g., carriage) that enables the C-arm to rotate in an orbital direction relative to the C-arm rotation device. The device is spring loaded (via a plurality of springs) into the C-arm (which also spring loads a brake roller assembly) to enable the device to apply both drag force and braking force on the C-arm that is consistent along the C-arm in an orbital direction regardless of variations in a cross-sectional profile of the C-arm in the orbital direction. The spring loaded roller acts as a clutch through its rolling resistance. In addition, the device includes a brake pad and roller (e.g., forming a portion of the brake roller assembly). When the device applies a braking force to the C-arm, the brake pad is configured to directly contact the roller and to not contact the C-arm. Thus, the braking force is applied via contact between tires coupled to the roller and the C-arm. The device provides a number of advantages over past devices for clutch and braking. First, the device is single unit or assembly (as opposed to a separate system for both the brake and the clutch), which simplifies the overall structure and, thus, assembly and manufacturing of the device. Second, the device is able to adapt to an imperfect C extrusion.

Figure 1:
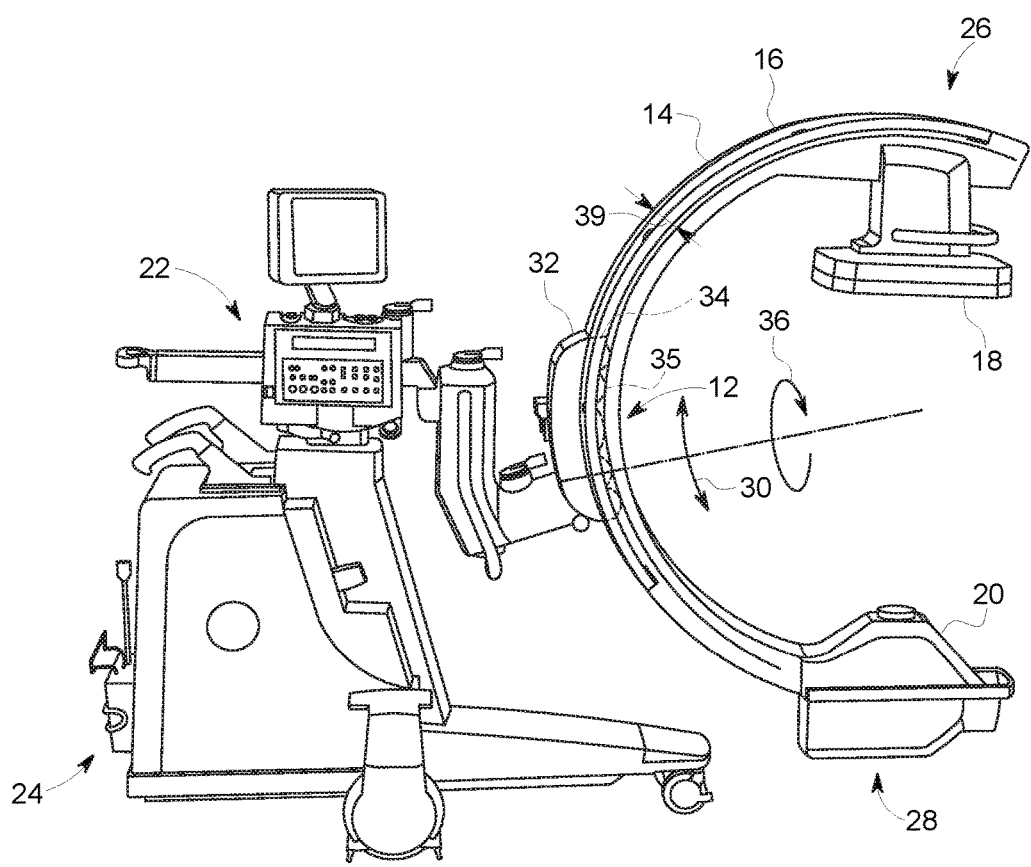
FIG. 1 is a side view of an embodiment of an X-ray imaging system (e.g., a mobile C-arm imaging system) having an orbital clutch and brake assembly.

FIG. 1 is a side view of an embodiment of an X-ray imaging system 10 (e.g., a mobile C-arm imaging system) having an orbital clutch and brake assembly 12. Although a mobile imaging system is illustrated, the embodiments described below may be utilized with any X-ray imaging system having a C-arm (e.g., a fixed imaging system). The system 10 includes a C-arm 16, an image receptor 18 (e.g., X-ray detector), an X-ray source 20, a support structure 22, and a wheeled base 24. The image receptor 18 and the X-ray source 20 are mounted at opposing locations (e.g., ends 26, 28) on the C-arm 16. The support structure 22 provides support for the C-arm 16 and holds the C-arm 16 in a suspended position. The support structure 22 is mounted on the wheeled base 24 that enables the system 10 to be moved.

The support structure 22 provides stable, balanced support for the C-arm 16. The support structure 22 suspends the C-arm 16 for use in imaging a patient or an object, for example. The support structure 22 also allows the C-arm 16 to be rotated about an axis of rotation (manually or using a motor, for example). For example, the C-arm 16 may be rotated in an orbital direction 30. As depicted, the support structure 22 includes a C-arm rotation device 32 (e.g., carriage or flip-flop) that enables the C-arm 16 to move or rotate in the orbital direction 30 along its track 14 relative to device 32. A portion 34 of the C-arm rotation device 32 (including wheels 35) is disposed within a track 14 to enable the C-arm 16 to move or rotate in the orbital direction 30. In certain embodiments, the C-arm rotation device 32 enables the C-arm to rotate or flip-flop (e.g., as indicated by reference numeral 36) about an axis 38 emanating from where the C-arm rotation device 32 is coupled to the C-arm 16. The support structure 22 is attached to the wheeled base 24, for example, to reposition the mobile C-arm imaging system 10.

As depicted, the orbital clutch and brake assembly 12 is coupled to (e.g., disposed within) the C-arm rotation device 32. As described in greater detail below, the orbital clutch and brake assembly 12 form a single unit or assembly configured to apply both a braking force and a clutch force to the C-arm 16. In particular, the assembly 12 consistently applies braking force and the clutch force to the C-arm 16 regardless of variations in a cross-sectional profile 39 (e.g., along track 14) of the C-arm 16 in the orbital direction 30. In addition, the braking force is applied via a brake pad contacting a roller of the assembly, where the brake does not contact the C-arm 16. Thus, the braking force is applied via contact between the tires of the roller and the C-arm 16.

The C-arm 16 allows the image receptor 18 and the X-ray source 20 to be mounted and positioned about an object to be imaged, such as a patient. The C-arm 16 may be a circular C-shaped or an arc-shaped member, for example. The C-arm 16 enables selective positioning of the image receptor 18 and the X-ray source 20 with respect to the width and length of the patient or other object located within the interior free space of the C-arm 16.

The image receptor 18 may be an image intensifier or other energy receptor for using in diagnostic imaging, for example. The image receptor 18 and the X-ray source 20 are mounted at opposing positions (e.g., ends 26, 28) on the C-arm 16. The image receptor 18 and the X-ray source 20 may be positioned about an object, such as a patient, using the C-arm 16 and support structure 22. The image receptor 18 and the X-ray source 20 are used to generate a diagnostic image representative of the object being imaged.

In operation, a patient, for example, is placed on a table that is positioned between the image receptor 18 and the X-ray source 20 mounted on the C-arm 16. The support structure 22 moves the C-arm 16. Moving the C-arm 16 positions the image receptor 18 and the X-ray source 20 at desired locations with respect to the patient. The image receptor 18 may be positioned near the patient in order to improve resulting image quality.

Figure 2:
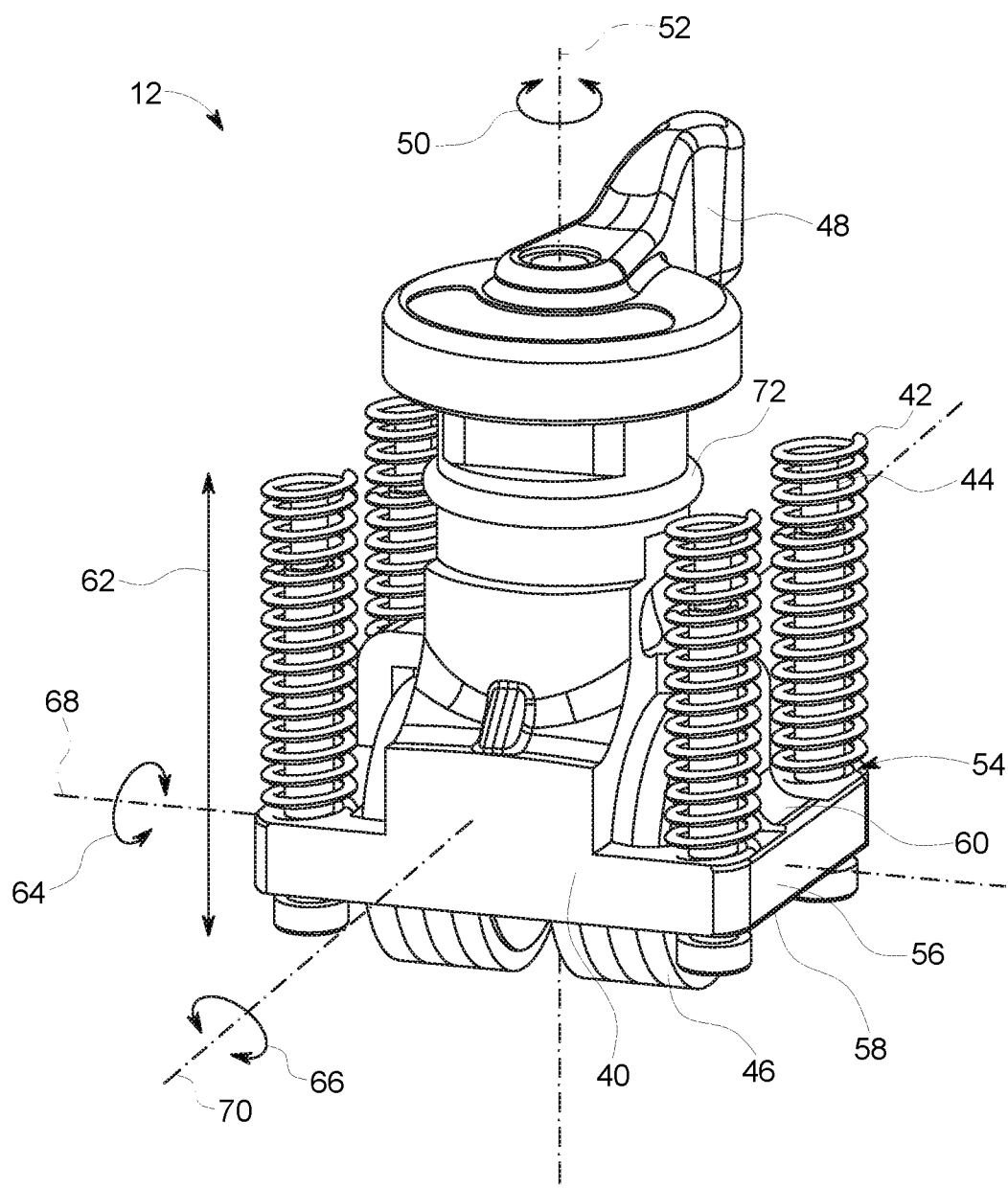
FIG. 2 is a perspective view of the orbital clutch and brake assembly of FIG. 1.

FIG. 2 is a perspective view of the orbital clutch and brake assembly 12 of FIG. 1. The orbital clutch and brake assembly 12 includes a housing 40 (e.g., carriage or body), a plurality of springs 42, a plurality of screws 44 (e.g., shoulder screws), tires 46, and a handle 48 (e.g., actuation handle). The housing 40 encloses a brake roller assembly that includes a roller coupled to the tires 46 and a brake pad. The brake roller assembly includes a shaft having a threaded portion. The threaded portion is coupled to the brake pad. The handle 48 is coupled to an end of the shaft opposite the threaded portion. The handle 48 is coupled to a castle having teeth. The handle 48 includes corresponding teeth that fit between the teeth on the castle. The castle is also disposed about the end of the shaft opposite the threaded portion. Actuation (e.g., circumferential rotation 50 relative to a longitudinal axis 52) of the handle 48 adjusts the position of the brake (via the shaft) relative to the roller. For example, complete circumferential rotation 50 in a first direction causes the brake pad to contact the roller to cause the roller (via the tires 46) to apply a braking force to the C-arm 16. The brake pad does not contact the C-arm 16. Complete circumferential rotation 50 in a second direction, opposite the first direction, causes the brake pad to no longer contact the roller. In certain embodiments, the handle 48 may be rotated up to approximately 75 degrees. The handle 48 may be rotated between 0 (no contact between brake pad and roller) and 75 degrees (contact between brake pad and roller with complete pressure applied) so that the brake pad contacts but applies less friction to the roller to result in a partial application of the braking force. For example, rotation of the handle to a first position in the first direction may cause the brake pad to contact the roller with a first amount of friction to apply a first braking force, while rotation of the handle to a second position in the first direction may cause the brake pad to contact the roller with a second amount of friction (e.g., less than the first amount of friction) to apply a second braking force (e.g., less than the second amount of friction).

As depicted, the plurality of screws 44 (e.g., shoulder screws) extend through respective openings 54 in a base portion 56 from a bottom surface 58 to a top surface 60. The screws 44 extend in a direction parallel with the longitudinal axis 52. As depicted, the plurality of screws 44 includes four screws 44. In other embodiments, the number of screws 44 may vary. Each spring 42 of the plurality of springs 42 is disposed about a respect screw 44. The springs 42 spring load the orbital clutch and brake assembly 12 (including brake roller assembly) into the C-arm 16. In addition, spring loading of the roller imparts a rolling resistance, which enables the spring loaded roller to act as a clutch via its rolling resistance. Since the roller is spring loaded, the loading force of the roller is consistent. The type of spring and/or the compressed length of the springs 42 may be changed to alter the loading of the orbital clutch and brake assembly 12 (including brake roller assembly) into the C-arm 16. In addition, altering the type of spring and/or the compressed length of the springs 42 changes the rolling resistance of the roller (and the tires 46), thus effecting the clutch (drag) force as well as how much force an operator must input to move the C-arm 16 in the orbital direction 30. The tires 46 are configured to deflect. The ability of the tires 46 to deflect and the spring loading of the entire assembly 12 enables the assembly 12 to apply both a drag force and/or a braking force on the C-arm 16 that is consistent along the C-arm 16 in the orbital direction 30 regardless of variations in the cross-sectional profile 39 or shape (e.g., along track 14) of the C-arm 16 in the orbital direction 30.

The assembly 12 (including brake roller assembly) translates or moves along the respective lengths of the screws 44 as indicated by arrow 62. The assembly 12 is not tightly controlled by the screws 44. As a result, the assembly 12 is configured to pitch 64, roll 50, and yaw 66 up to approximately 5 degrees relative to each respective axis 68, 52, 70. In addition, when a sudden impact force is applied to the C-arm 16, the assembly 12 bounces (e.g., radially relative to the C-arm 16) for a given period of time (e.g., approximately 30 seconds). The ability of the assembly 12 to pitch 64, roll 50, and yaw 66 dampens out the vibrations. The ability of the assembly 12 to dampen out the vibrations is dependent of the assembly's fit to the screws 44 and the fit/durometer of a debris seal O-ring 72. The O-ring 72 is disposed about a cylindrical portion of the housing 40 and contacts a portion of the C-arm rotation device 32.

The structure and function of the assembly 12 makes user input (e.g., to apply the brake) and the effectiveness of the brake consistent across different systems that utilize a C-arm 16. The assembly 12 also reduces the force utilized by an operator to actuate the brake. The assembly 12 is easy to use, requires minimal maintenance, and is quick and easy to adjust.

Figure 3:
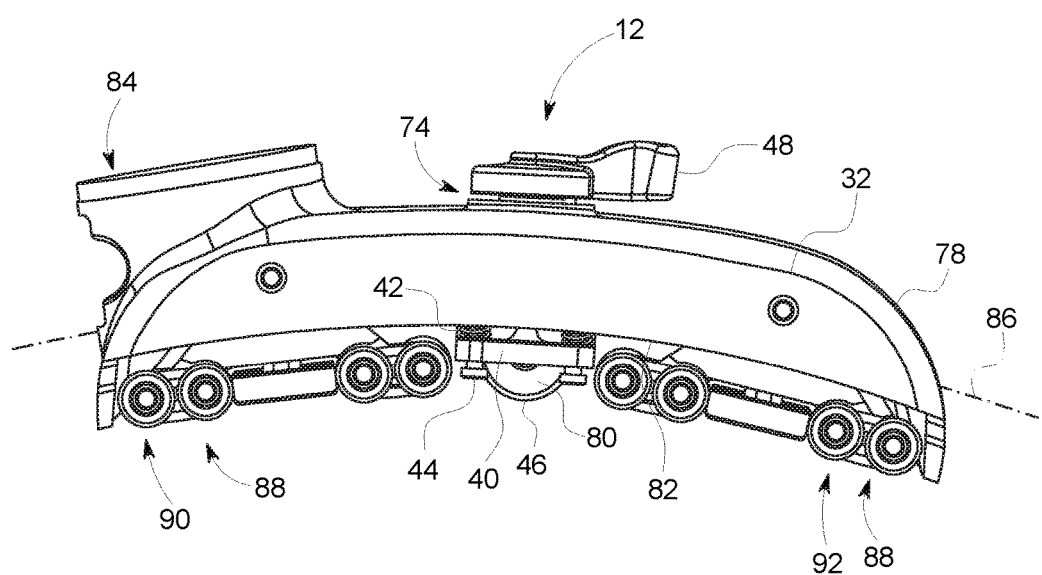
FIG. 3 is a side view of the orbital clutch and brake assembly of FIG. 1 coupled to a C-arm arm rotation device.

FIG. 3 is a side view of the orbital clutch and brake assembly 12 of FIG. 1 coupled to the C-arm arm rotation device 32. The assembly 12 is as described above. As depicted, a portion of the assembly 12 is disposed within the C-arm rotation device 32. The assembly 12 extends through an opening 74 of the C-arm rotation device 32. The handle 48 is disposed outside of a top surface 76 of a body portion 78 of the C-arm rotation device 32. Portions of the assembly 12 (e.g., tires 46 coupled to the roller 80, housing 40, springs 42, and screws 44 extend beyond a bottom surface 82 of the body portion 78 of the C-arm rotation device 32. The body portion 78 also includes an opening 84 (e.g., axially offset from the opening 74 relative to a longitudinal axis 86 of the C-arm rotation device 32) that enables the C-arm rotation device 32 to couple to the imaging system 10 (e.g., via support structure 22). The C-arm rotation device 32 enables the C-arm to rotate or flip-flop (e.g., as indicated by reference numeral 36) about the axis 38 emanating from where the C-arm rotation device 32 is coupled to the C-arm 16 (see FIG. 1) at the opening 84. As depicted, the C-arm rotation device 32 includes a plurality of rollers or wheels 88 to enable the C-arm rotation device 32 to move along the track 14 in the C-arm 16 in the orbital direction 30. In particular, the plurality of rollers 88 includes a first set of rollers 90 and a second set of rollers 92 flanking the assembly 12.

Figure 4:
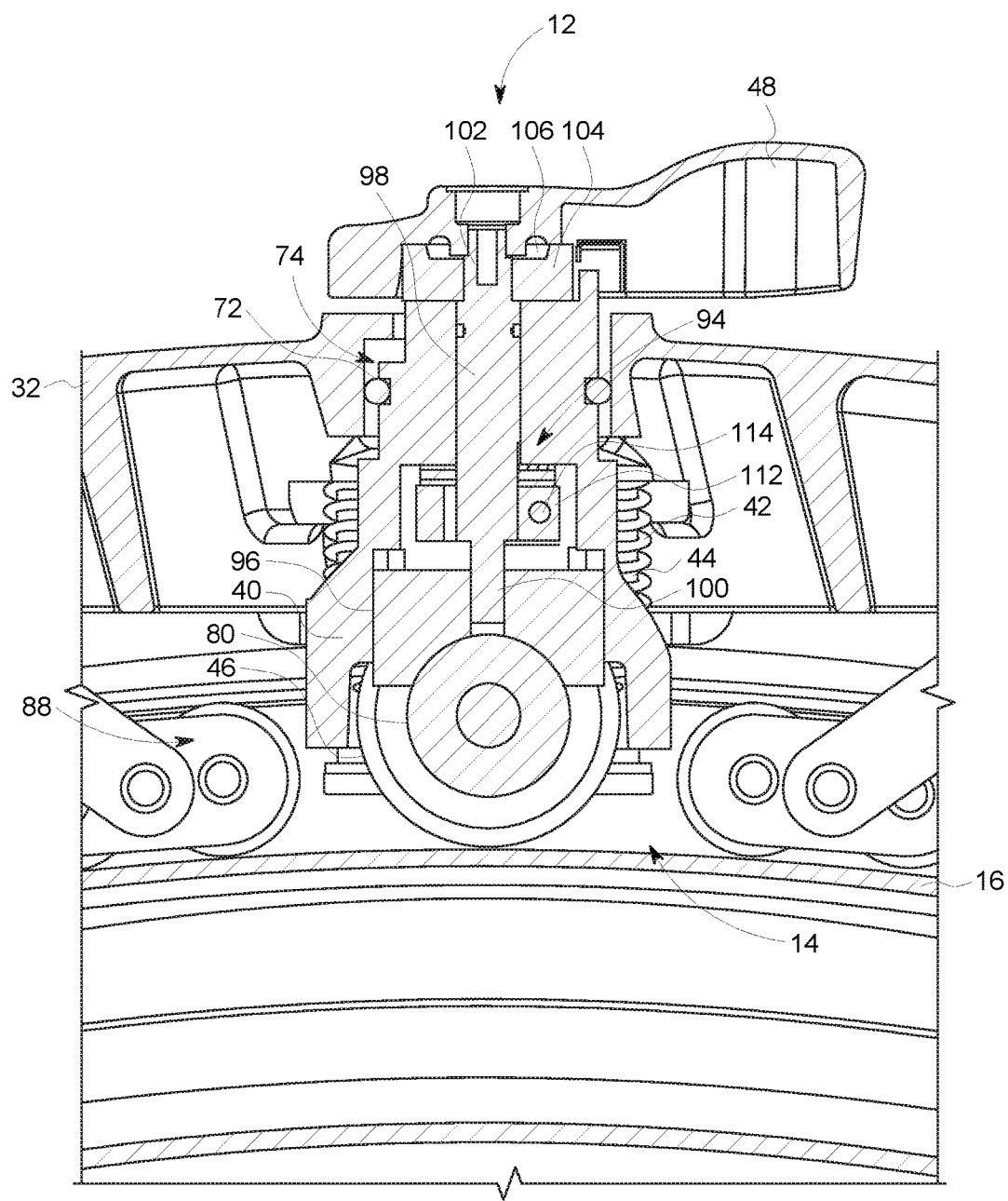
FIG. 4 is a cross-sectional side view of the orbital clutch and brake assembly and C-arm rotation device of FIG. 3 (e.g., illustrating brake roller assembly)
Figure 5:
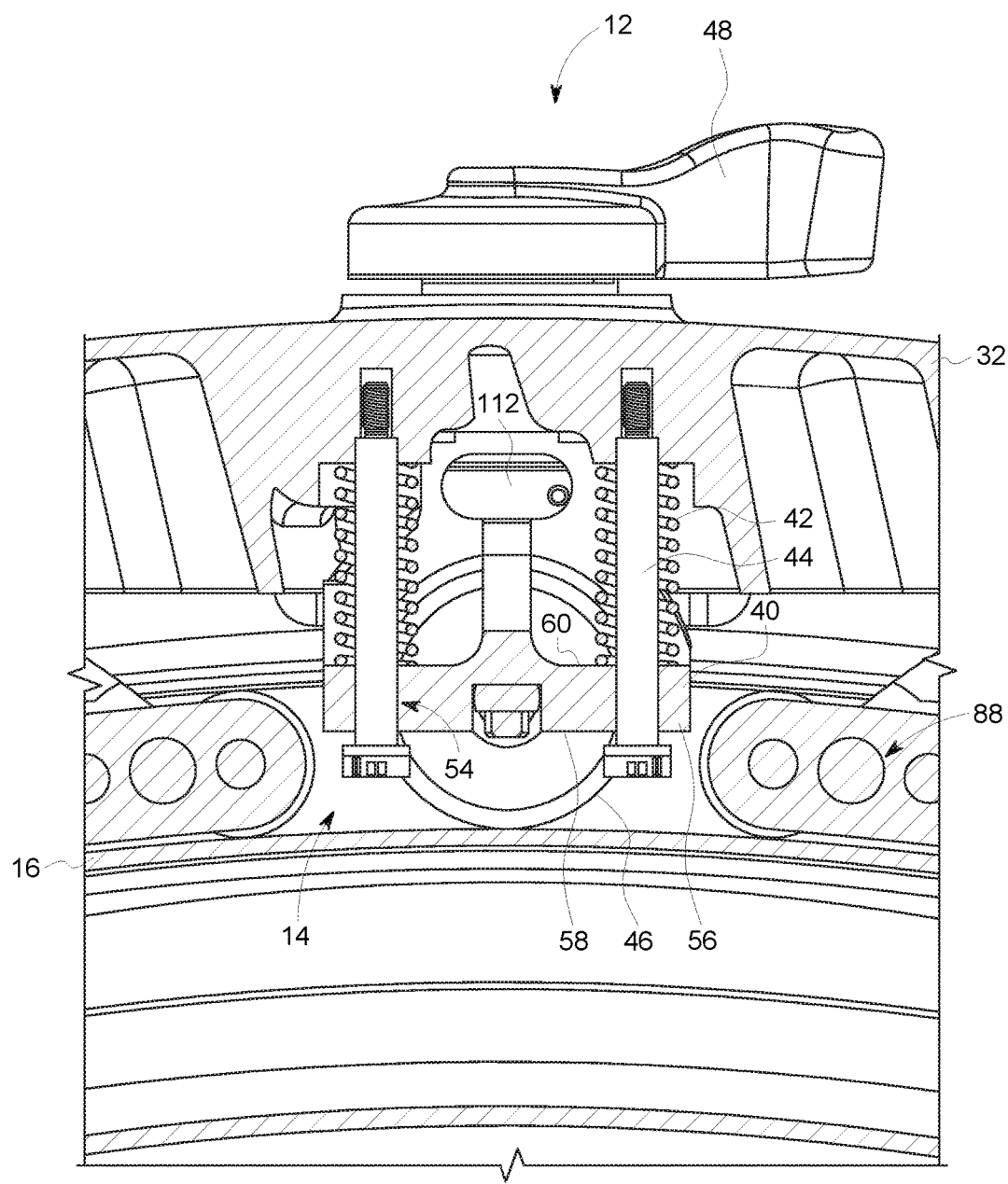
FIG. 5 is a cross-sectional side view of the orbital clutch and brake assembly and C-arm rotation device of FIG. 3 (e.g., illustrating springs and screws)
Figure 6:
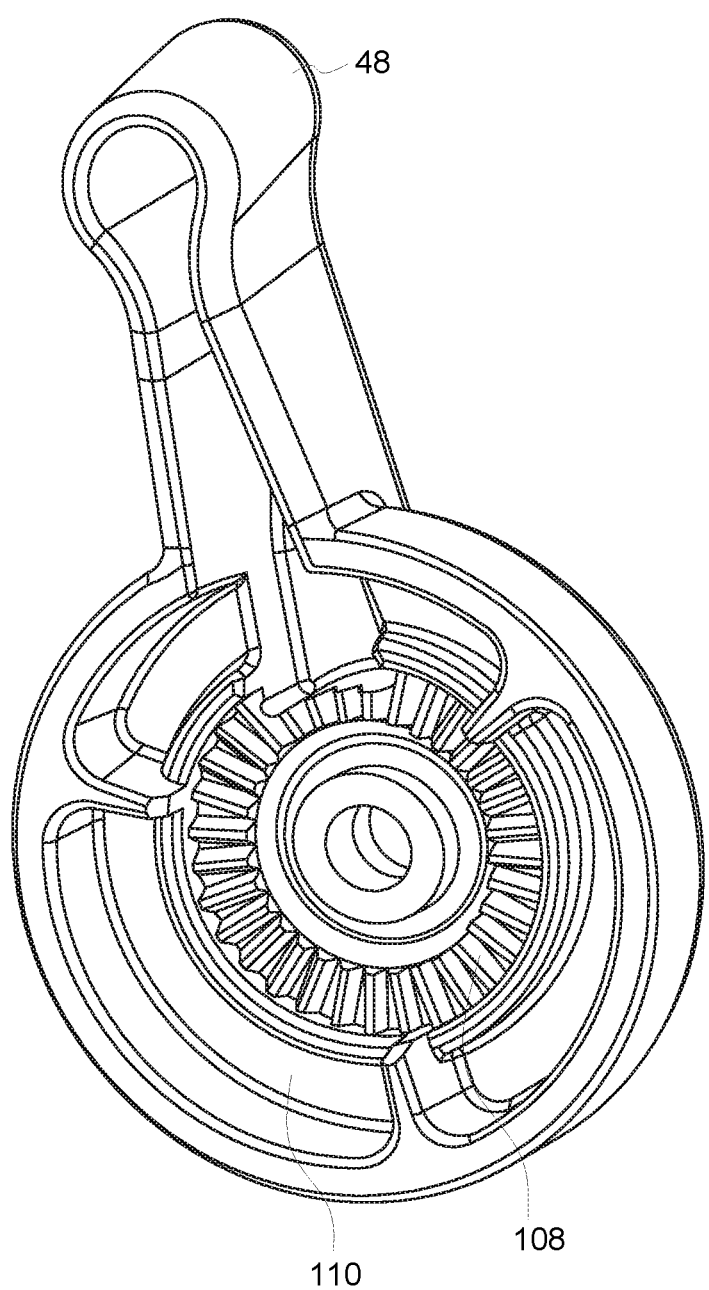
FIG. 6 is a perspective view of an inner surface of a handle of the orbital clutch and brake assembly of FIG. 1.

FIGS. 4 and 5 are different cross-sectional side views of the orbital clutch and brake assembly 12 and C-arm rotation device 32 of FIG. 3. In general, the assembly 12 and C-arm rotation device 32 are as described above. The housing 40 encloses a brake roller assembly 94 that includes the roller 80 (e.g., coupled to the tires 46) and a brake pad 96. The brake roller assembly 94 includes a shaft 98 having a threaded portion 100. The threaded portion 100 is coupled to (e.g., partially disposed within and interfacing with a corresponding threaded portion) the brake pad 96. The handle 48 is coupled to an end 102 of the shaft 98 opposite the threaded portion 100. The handle 48 is coupled to a castle 104 having teeth 106. In certain embodiments, the handle 48 includes corresponding teeth 108 on an inner surface 110 (see FIG. 6) that fit between the teeth 106 on the castle 104. The castle 104 is also disposed about the end 102 of the shaft 98 opposite the threaded portion 100. The castle 104 and the shaft 98 may be manufactured together as a single unit.

The brake roller assembly 94 may include other components (e.g., washers, needle bearing, etc.) that enable the castle 104 to be adjusted (e.g., due to wear). The brake roller assembly 94 is kept assembled via a split collar 112 held together via a fastener 114. The load is pushed into the collar 112. In certain embodiments, the O-ring 72 is disposed about a cylindrical portion of the housing 40 and contacts a portion of the C-arm rotation device 32. The O-ring 72 minimizes rocking of the assembly within the C-arm rotation device 32.

In certain embodiments, the roller 80 may be made of any hard material that does not gall. In certain embodiments, the roller 80 may be made of hard anodized aluminum. In certain embodiments, the brake pad 96 may be nickel plated.

Actuation (e.g., circumferential rotation 50 relative to a longitudinal axis 52, see FIG. 2) of the handle 48 adjusts the position of the brake pad 96 (via movement along the threaded portion 100 of the shaft 98) relative to the roller 80. For example, complete circumferential rotation 50 in a first direction causes the brake pad 96 to contact the roller 80 (as shown in FIG. 4) to cause the roller 80 (via the tires 46) to apply a braking force to the C-arm 16. The brake pad 96 does not contact the C-arm 16. Complete circumferential rotation 50 in a second direction, opposite the first direction, causes the brake pad 96 to no longer contact the roller 80. In certain embodiments, the handle 48 may be rotated up to approximately 75 degrees. The handle 48 may be rotated between 0 (no contact between brake pad 96 and roller 80) and 75 degrees (contact between brake pad 96 and roller 80 with complete pressure applied) so that the brake pad 96 contacts but applies less friction to the roller 80 to result in a partial application of the braking force.

As depicted, the plurality of screws 44 (e.g., shoulder screws) extend through respective openings 54 in a base portion 56 from a bottom surface 58 to a top surface 60. The screws 44 extend in a direction parallel with the longitudinal axis 52. The assembly 12 (including brake roller assembly 94) translates or moves along the respective lengths of the screws 44. Each spring 42 of the plurality of springs 42 is disposed about a respect screw 44. The springs 42 spring load the orbital clutch and brake assembly 12 (including brake roller assembly 94) into the C-arm 16. In addition, spring loading of the roller 80 imparts a rolling resistance, which enables the spring loaded roller 80 (via tires 46) to act as a clutch via its rolling resistance (e.g., due to contact pressure). Since the roller 80 is spring loaded, the loading force of the roller 80 is consistent. The type of spring and/or the compressed length of the springs 42 may be changed to alter the loading of the orbital clutch and brake assembly 12 (including brake roller assembly 94) into the C-arm 16. In addition, altering the type of spring and/or the compressed length of the springs 42 changes the rolling resistance of the roller 80 (and the tires 46), thus effecting the clutch (drag) force as well as how much force an operator must input to move the C-arm 16 in the orbital direction 30. The tires 46 are configured to deflect. The ability of the tires 46 to deflect and the spring loading of the entire assembly 12 enables the assembly apply both a drag force and/or a braking force on the C-arm 16 that is consistent along the C-arm 16 in the orbital direction 30 regardless of variations in the cross-sectional profile 39 or shape of the C-arm 16 in the orbital direction 30.

Technical effects of the disclosed embodiments include providing an orbital clutch and brake assembly in a single system or assembly that provides both a braking force and a clutch force to the C-arm of the X-ray imaging system. The assembly is spring loaded into the C-arm and is configured to apply both the braking force and the clutch force consistently along the C-arm regardless of variations in a cross-sectional profile of the C-arm (e.g., track) in the orbital direction. The structure and function of the assembly 12 makes user input (e.g., to apply the brake) and the effectiveness of the brake consistent across different systems that utilize a C-arm 16. The assembly 12 also reduces the force utilized by an operator to actuate the brake. The assembly 12 is easy to use, requires minimal maintenance, and is quick and easy to adjust.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray imaging system, comprising:
    an X-ray radiation source;
    an X-ray detector;
    a C-arm having the X-ray radiation source disposed on a first end and the X-ray detector disposed on a second end opposite the first end;
    a C-arm rotation device configured to enable the C-arm to rotate in an orbital direction relative to the C-arm rotation device; and
    an orbital clutch and brake assembly coupled to the C-arm rotation device, wherein the orbital clutch and brake assembly is spring loaded into the C-arm and configured to apply both a drag force and a braking force on the C-arm that is consistent along the C-arm in the orbital direction regardless of variations in a cross-sectional profile of the C-arm in the orbital direction, wherein the orbital clutch and brake assembly comprises a spring loaded roller which acts as a clutch via its rolling resistance, and the orbital clutch and brake assembly comprises a brake pad, and wherein the brake pad is configured to directly contact the roller and to not contact the C-arm when the braking force is applied.

2. The X-ray imaging system of claim 1, wherein the orbital clutch and brake assembly is partially disposed within the C-arm rotation device.

3. The X-ray imaging system of claim 1, wherein the orbital clutch and brake assembly comprises a shaft having a threaded portion, the shaft is coupled to the brake pad via the threaded portion, rotation of the shaft in a first direction is configured to cause the brake pad to contact the roller to apply the braking force, and rotation of the shaft in a second direction is configured to cause the brake pad to not contact the roller.

4. The X-ray imaging system of claim 3, wherein the orbital clutch and brake assembly comprises a housing, and the roller, the brake pad, and the shaft are disposed within the housing.

5. The X-ray imaging system of claim 4, wherein the orbital clutch and brake assembly comprises a plurality of screws disposed on an outside of the housing configured to enable the orbital clutch and brake assembly to move in a direction along respective lengths of the plurality of screws.

6. The X-ray imaging system of claim 5, wherein the orbital clutch and brake assembly comprises a plurality of springs, each spring of the plurality of springs being disposed about a respective screw of the plurality of screws, and the plurality of springs is configured to spring load the orbital clutch and brake assembly.

7. The X-ray imaging system of claim 3, wherein the shaft is configured to be rotated to a first position in the first direction to cause the brake pad to contact the roller with a first amount of friction to apply a first braking force, the shaft is configured to be rotated to a second position in the first direction to cause the brake pad to contact the roller with a second amount of friction to apply a second braking force, the first amount of friction is greater than the second amount of friction, and the first braking force is greater than the second braking force.

8. A device, comprises:
    an orbital clutch and brake assembly configured to couple to a C-arm rotation device that enables the C-arm to rotate in an orbital direction relative to the C-arm rotation device, wherein the orbital clutch and brake assembly comprises:
        a housing;
        a roller;
        a brake pad, wherein the roller and brake pad are disposed within the housing, and the brake pad is configured to directly contact the roller and to not contact the C-arm when the orbital clutch and brake assembly applies a braking force to the C; arm; and
        a shaft having a threaded portion, the shaft is coupled to the brake pad via the threaded portion, rotation of the shaft in a first direction is configured to cause the brake pad to contact the roller to apply the braking force, and rotation of the shaft in a second direction is configured to cause the brake pad to not contact the roller.

9. The device of claim 8, comprising a plurality of springs disposed on an outside of the housing, and the plurality of springs is configured to spring load the orbital clutch and brake assembly into the C-arm and to apply both a drag force and the braking force on the C-arm that is consistent along the C-arm in the orbital direction regardless of variations in a cross-sectional profile of the C-arm in the orbital direction.

10. The device of claim 9, wherein the plurality of springs is configured to spring load the roller so that roller acts as a clutch via its rolling resistance.

11. The device of claim 9, wherein the orbital clutch and brake assembly comprises a plurality of screws disposed on an outside of the housing configured to enable the orbital clutch and brake assembly to move in a direction along respective lengths of the plurality of screws.

12. The device of claim 11, wherein the orbital clutch and brake assembly comprises a plurality of screws disposed on the outside of the housing configured to enable the orbital clutch and brake assembly to move in a direction along respective lengths of the plurality of screws.

13. The device of claim 12, each spring of the plurality of springs is disposed about a respective screw of the plurality of screws.

14. The device of claim 8, wherein the shaft is configured to be rotated to a first position in the first direction to cause the brake pad to contact the roller with a first amount of friction to apply a first braking force, the shaft is configured to be rotated to a second position in the first direction to cause the brake pad to contact the roller with a second amount of friction to apply a second braking force, the first amount of friction is greater than the second amount of friction, and the first braking force is greater than the second braking force.

15. A device, comprises:
an orbital clutch and brake assembly configured to couple to a C-arm rotation device that enables the C-arm to rotate in an orbital direction relative to the C-arm rotation device, wherein the orbital clutch and brake assembly comprises:
a housing;
a plurality of springs;
a roller; and
a brake pad, wherein the roller and brake pad are disposed within the housing, the plurality of springs are disposed on an outside of the housing, and the plurality of springs is configured to spring load the orbital clutch and brake assembly into the C-arm to enable the orbital clutch and brake assembly to apply both a drag force and a braking force on the C-arm that is consistent along the C-arm in the orbital direction regardless of variations in a cross-sectional profile of the C-arm in the orbital direction.

16. The device of claim 15, wherein the plurality of springs is configured to spring load the roller so that roller acts as a clutch via its rolling resistance.

17. The device of claim 15, wherein the brake pad is configured to directly contact the roller and to not contact the C-arm when the orbital clutch and brake assembly applies the braking force to the C-arm.

* * * * *